United States Patent

Baust et al.

[11] Patent Number: 6,056,948
[45] Date of Patent: May 2, 2000

[54] EXTRA-MILD SHOWER GEL AND HAIR SHAMPOO FORMULATION WITH LOW TENSIDE CONCENTRATION

[75] Inventors: Heinrich Baust, Plankstadt; Guido Waeschenbach, Mannheim, both of Germany

[73] Assignee: Benckiser N.V., Luchthaven Schiphol, Netherlands

[21] Appl. No.: 07/960,420

[22] PCT Filed: Jun. 8, 1991

[86] PCT No.: PCT/EP91/01077

§ 371 Date: Dec. 23, 1992

§ 102(e) Date: Dec. 23, 1992

[87] PCT Pub. No.: WO92/00058

PCT Pub. Date: Jan. 9, 1992

[30] Foreign Application Priority Data

Jun. 27, 1990 [DE] Germany .............................. 40 20 500

[51] Int. Cl.[7] ................................ A61K 6/00; A61K 7/00; A61K 7/06
[52] U.S. Cl. .................... 424/70.19; 424/401; 424/70.21; 424/70.22; 424/70.24; 424/70.27; 424/70.28
[58] Field of Search ............................ 424/70, 71, 70.24, 424/70.28, 70.19, 70.21, 70.22, 401

[56] References Cited

U.S. PATENT DOCUMENTS

| | | | |
|---|---|---|---|
| 3,990,991 | 11/1976 | Gerstein | 252/542 |
| 4,148,762 | 4/1979 | Koch | 252/544 |
| 4,329,334 | 5/1982 | Su | 424/70 |
| 4,490,355 | 12/1984 | Desai | 424/70 |
| 4,670,253 | 6/1987 | Ploog | 424/70 |
| 4,900,544 | 2/1990 | Ritter | 424/70 |

FOREIGN PATENT DOCUMENTS

| | | |
|---|---|---|
| 0 099 987 | 6/1983 | European Pat. Off. . |
| 0 236 677 | 1/1987 | European Pat. Off. . |
| 0 417 501 | 8/1990 | European Pat. Off. . |
| 3910652 | 4/1989 | Germany . |
| 2 219 594 | 5/1989 | United Kingdom . |

OTHER PUBLICATIONS

Paassen, "Alkylethercarboxylate: Hautfreundliche Rohstoffe für kosmetische Anwendungen", Seifen, Öle, Wachse (1983) pp. 353–355. (ul. at p. 2 of spec.—No translation).

*Primary Examiner*—Thurman K. Page
*Assistant Examiner*—Sharon Howard
*Attorney, Agent, or Firm*—Foley & Lardner

[57] ABSTRACT

The invention relates to novel shower gels and hair shampoos containing a neutralised tenside combination of alkyl polyglycol ether carboxylate, alkyl ether sulphate and fatty acid amidopropyl betaine and the customary auxiliary and base substances which the average degree of ethoxylation of the alkyl polyglycol ether carboxylate is 2–5.

13 Claims, No Drawings

EXTRA-MILD SHOWER GEL AND HAIR SHAMPOO FORMULATION WITH LOW TENSIDE CONCENTRATION

The present invention relates to a new extra-mild shower gel and hair shampoo formulation with low tenside concentration.

The production quantity of shower baths and hair shampoos in the cosmetics industry in Germany is currently about 110,000 tonnes per year. The tenside content of the commercially available products here is between 15 and 25%. About 20,000 tonnes per year of tensides thus pass into waste waters, where they are degraded more or less quickly and completely. A reduction in the washing-active substances is an aim worth pursuing from both the economic and the ecological aspect.

It is known that certain tensides, and thus also those containing ether-sulfates, having a very pronounced foam formation allow a drastic reduction in washing-active substances from, for example, 20% to 10%, but therefore, in contrast to other tensides, cause a lower viscosity of the mixture. The decrease in viscosity which occurs must be compensated by electrolyte additions (NaCl, $Na_2SO_4$) which pollute the waste waters, or organic thickeners which additionally pollute the waste water. The salt load easily exceeds the tenside concentration here, which significantly increases on the one hand the risk of burning of the eyes, and on the other hand the instability (salting out effect).

There was therefore the object of discovering a mild tenside combination for skin and hair care which contains ether-sulfate and has good foaming properties, with which highly viscous formulations can be prepared at tenside concentrations of less than 10% with a minimum of electrolyte salts and without additional thickeners. The products furthermore should have a good biological degradability, so that they do not pollute the environment.

Surprisingly, this object is achieved or promoted by the features characterized in more detail in the claims.

It is known from the earlier application, which has not previously been published, P 39 10 652.7 that a tenside combination of lauryl polyglycol ether-carboxylate, lauryl sulfate and lauric acid amidopropylbetaine can be processed with 2–10% of sodium chloride to give a shower gel which is tolerated well. The lauryl glycol ether-carboxylate used here had a degree of ethoxylation of 8–10 ethoxy groups. In order to produce adequate foaming properties, a total tenside concentration of 15–20% was necessary. 4.5% of NaCl was added to adjust the viscosity.

Alkyl ether-carboxylic acids having a lower degree of ethoxylation (2–5) are not employed in body cleansing agents, in spite of their good tenside action, because of the eye and skin irritations which thereby occur (Seifen, Ole, Wachse (1983) pages 353–355).

Surprisingly, the alkyl ether-carboxylic acids having a low degree of ethoxylation (2–5), which are more aggressive when used by themselves, no longer exhibit skin irritations in the combination according to the invention, and have such a high foam formation capacity that total tenside concentrations of less than 10% are possible.

Alkyl polyglycol ether-carboxylic acids in the context of the invention are compounds of the formula I $$R\text{—}O\text{—}(CH_2\text{—}CH_2\text{—}O)_n\text{—}CH_2\text{—}CO_2H \qquad (I)$$

in which R denotes an alkyl group having 8 to 20 C atoms, preferably 10–16, in particular 12–14 C atoms, and n denotes a natural number from 2 to 5, preferably 2.5. The carboxylic acids are preferably neutralized with sodium, potassium or ammonium ions, in particular tris (hydroxymethyl)aminomethane.

During customary preparation of the compounds I by polycondensation of fatty alcohols with ethylene oxide (ethoxylation) and subsequent reaction with monochloroacetic acid, mixtures are formed which are separated only roughly, if at all, for use as a tenside. The number n is therefore to be understood as the mean value of the compounds contained in the mixture. The mixture can also still contain certain amounts of unreacted fatty alcohol ethoxylates.

Alkyl ether-sulfates in the context of the invention are ethoxylated sulfuric acid monoalkyl esters which are derived from fatty alcohols which are well-known as tensides, and have particularly good foaming properties under hard water conditions.

The degree of ethoxylation is on average 2–8, preferably 2–5. The end group is a linear alkyl group having 8–20, preferably 10–18 C atoms. Lauryl and coconut fatty alcohol groups are preferred for economic reasons. The ratio of fatty alcohol ether-sulfate to alkyl polyglycol ether carboxylate is 1:0.25 to 1.5, and that of fatty alcohol ether-sulfate to fatty acid amidopropyl-betaine preferably is 1:0.15 to 1.0.

Fatty acid amidopropylbetaines are likewise well-known as tensides. Customary fatty acids are those having 8–20, in particular 12–14 C atoms. Laurylamidopropylbetaine is preferred because of the optimum foaming properties and the interaction with the other two components for the purpose of good thickening, without a sparingly soluble precipitate being formed at lower temperatures.

Another advantage of the mixtures according to the invention is that they can be formulated without protein, since the amino acid mixtures known here can also be allergenic. The use of lauric acid monoglyceride, together with the tenside mixture according to the invention, is proposed as an oil-restoring component.

The use of lauryl alcohol ethoxylate has proved to be particularly appropriate for solubilizing perfume oils usually employed in such skin cleansing agents, since this agent renders oil particularly readily soluble.

A shower gel such as can preferably be prepared with the aid of the abovementioned substances comprises, in addition to the perfume oil already mentioned, sodium chloride as a thickening agent and/or the polyfunctional active compound Na hexametaphosphate. Furthermore, substances for preservation, for example dibromocyanobutane/ phenoxyethanol (Euxyl K 400, trademark of Schuhlke u. Mayr) and water.

Conditioners, in particular quaternized copolymers, such as dimethylalkylammonium chloride polymer (Merquat 550, trademark of Merck & Co. Inc.), vinylpyrrolidone/ dimethylaminoethyl methacrylate (Gafquad 734— trademark of General Aniline Film Co.) or Miropol A 15 (trademark of Miranal Chem. Co. Inc.) are also employed in amounts of up to 2%, in particular 0.2–1%, to improve the properties, especially in hair shampoos. Neutralizing agents such as KOH, NaOH and tris-(hydroxymethyl)- aminomethane (TRIS) also may be added to the shower gel and hair shampoo composition to achieve a pH of 5.5–7.5. The shower gel and hair shampoo composition also can include conditioners, protein hydrolyzates and/or acrylamide polymers as well as electrolytes such as sodium chloride and thickeners such as polyphosphates, particularly sodium hexametaphosphate.

Shower gels having a composition according to the invention preferably contain the following proportions (% by weight)

| | |
|---|---|
| Alkyl polyglycol ether-carboxylate | 2.0–5 |
| Fatty alcohol ether-sulfate | 2.0–7 |
| Fatty acid amidopropyl-betaine | 1.0–3 |
| Protein hydrolyzate | 0.3–1.5 |
| Lauryl alcohol ethoxylate | 0.1–0.5 |
| Conditioner | 0–2 |
| Perfume | 0.5–2 |
| Na hexametaphosphate | 0–5 |
| NaCl | 2–10 |
| Preservative | 0.05–0.5 |
| Water | to 100 |

EMBODIMENT EXAMPLES

Example 1

10% Strength WAS Shower Gel

| | C % |
|---|---|
| C12/14 ether-carboxylic acid, 2.5 mol of EO, Na salt | 4.27 |
| Sodium lauryl diglycol ether-sulfate | 3.25 |
| Lauric acid amidopropylbetaine | 2.53 |
| Perfume oil | 0.72 |
| Preservative (Euxyl K 400 *) | 0.07 |
| NaCl | about 2.00 |
| Water, sterilized | to 100 |

* Trademark of Schühlke und Mayr
pH brought to pH 6.5–6.8 with NaOH or TRIS

Example 2

8% WAS Shower Gel

| | C % |
|---|---|
| C 12/14 ether-carboxylic acid, 2.5 mol of EO Na salt | 3.39 |
| C 12/14 alkyl ether-sulfate, 3.5 mol of EO Na salt | 2.58 |
| C 12/14 fatty acid amidopropylbetaine | 2.01 |
| Protein hydrolyzate | 0.72 |
| Glycerol partial ester, ethoxylated | 0.26 |
| Perfume oil | 0.57 |
| Dyestuffs | q.s. |
| Preservative | 0.07 |
| NaCl | about 2.00 |
| Water, sterilized | to 100 | pH brought to pH 6.5–6.8 with NaOH or TRIS

Example 3

10% Strength WAS Hair Shampoo

| | C % |
|---|---|
| Lauryl ether-carboxylic acid, 2.5 mol of EO (Na salt) | 4.27 |
| Fatty alcohol ether-sulfate * | 3.25 |
| Fatty acid amidopropylbetaine * | 2.53 |
| Protein hydrolyzate | 0.91 |
| Glycerol partial ester, ethoxylated | 0.32 |
| Perfume oil | 0.50 |
| Dyestuffs | q.s. |
| Preservative | 0.07 |
| NaCl | about 2.00 |
| Water, sterilized | to 100 |

(* R = coconut or lauryl)
pH brought to pH 6.5–6.8 with NaOH or TRIS

Example 4

8% WAS Hair Shampoo

| | C % |
|---|---|
| C 12/14 ether-carboxylic acid, 2.5 mol of EO Na salt | 3.32 |
| Fatty alcohol ether-sulfate * | 2.58 |
| Fatty acid amidopropylbetaine * | 2.01 |
| Protein hydrolyzate | 0.72 |
| Preservative | 0.07 |
| Glycerol partial ester, ethoxylated | 0.26 |
| Perfume oil | 0.57 |
| Dyestuffs | q.s. |
| Euxyl K 400 | 0.07 |
| NaCl | about 2.00 |
| Water, sterilized | to 100 |

(* R = coconut or lauryl)
pH brought to pH 6.5–6.8 with NaOH or TRIS

Example 5

10% WAS Shower Gel

| | C % |
|---|---|
| C 12/14 fatty alcohol ether-sulfate, 2 mol of EO, Na salt | 6.25 |
| C 12/14 ether-carboxylic acid, 2.5 mol of EO, Na salt | 2.41 |
| Fatty acid amidopropylbetaine* | 1.19 |
| Protein hydrolyzate | 0.44 |
| Glycerol partial ester, ethoxylated | 0.28 |
| Perfume oil | 0.75 |
| Diglycol stearate** | about 0.50 |
| Dyestuffs | q.s. |
| Preservative | 0.07 |
| NaCl | about 2.65 |
| Water, sterilized | to 100 |

*(R = coconut or lauryl)
Ph [sic] brought to pH 6.5–6.8 with NaOH or TRIS
**for pearlescent products

We claim:

1. A shower gel and hair shampoo composition comprising a neutralized tenside combination of alkyl polyglycol ether-carboxylate, fatty alcohol ether-sulfate and fatty acid amidopropyl-betaine, wherein the alkyl polyglycol ether-carboxylic acid used has the general formula I $$R-O-(CH_2CH_2O)_n CH_2COOH \qquad (I)$$

in which R denotes a straight-chain alkyl group having 8–20 carbon atoms and n denotes on average 2 to 5, and wherein the ratio of fatty alcohol ether-sulfate to alkl polyglycol ether carboxylate is 1:0.25 to 1.5, and that of fatty alcohol ether-sulfate to fatty acid amidopropyl-betaine is 1:0.15 to 1.0.

2. A shower gel and hair shampoo according to claim 1, wherein the average degree of ethoxylation of the alkyl polyglycol ether-carboxylates is 2.5.

3. A shower gel and hair shampoo according to claim 1, wherein the composition has a pH of 5.5–7.5, and further comprises KOH as a neutralizing agent.

4. A shower gel and hair shampoo according to claim 1, wherein the total tenside concentration is 10% or less.

5. A shower gel and hair shampoo according to claim 1, wherein they contain lauryl alcohol-ethoxylate.

6. A shower gel and hair shampoo according to claim 1, wherein they comprise conditioners, protein hydrolyzates and/or acrylamide polymers.

7. A shower gel and hair shampoo according to claim 1, further comprising an electrolyte salt, or a polyphosphate as a thickener.

8. A shower gel and hair shampoo according to claim 1, wherein the composition comprises the following in % by weight;

| | |
|---|---|
| Alkyl polyglycol ether-carboxylate | 2–5 |
| Fatty alcohol ether-sulfate | 2–7 |
| Fatty acid amidopropyl-betaine | 1–3 |
| Protein hydrolyzate | 0.3–1.5 |
| Lauryl alcohol-ethoxylate | 0.1–0.5 |
| Conditioner | 0–2 |
| Perfume | 0.5–2 |
| Na hexametaphosphate | 0–5 |
| NaCl | 2–10 |
| Preservative | 0.05–0.5 |
| Water | to 100 |

9. A shower gel and hair shampoo composition comprising:

a) a viscous, aqueous solution of a neutralized surfactant combination of alkyl polyglycol ether-carboxylate, fatty alcohol ether-sulfate and fatty acid amidopropyl-betaine, wherein the alkyl polyglycol ether-carboxylic acid used has the general formula I $$R\text{—}O\text{—}(CH_2CH_2O)_n\,CH_2COOH \qquad (I)$$

in which R denotes a straight-chain alkyl group having 8–20 carbon atoms and n denotes on average 2 to 5, and is present in an amount of about 2–5% by weight, the fatty alcohol ether-sulfate is present in an amount of 2–7% by weight, the fatty acid amidopropyl-betaine is present in an amount of 1–3% by weight, and the total concentration of tensides is less than 10% by weight; and b) electrolyte salts which are present in an amount of 2–10% by weight, wherein the composition is prepared without addition of thickeners.

10. A shower gel and hair shampoo composition according to claim 1, wherein the composition further comprises NaOH as a neutralizing agent.

11. A shower gel and hair shampoo composition according to claim 1, wherein the composition comprises tris-(hydroxymethyl)-aminoethane as a neutralizing agent.

12. A shower gel and hair shampoo composition according to claim 7, wherein the electrolyte salt is sodium chloride.

13. A shower gel and hair shampoo composition according to claim 7, wherein the polyphosphate is sodium hexametaphosphate.

* * * * *